Figure 1:
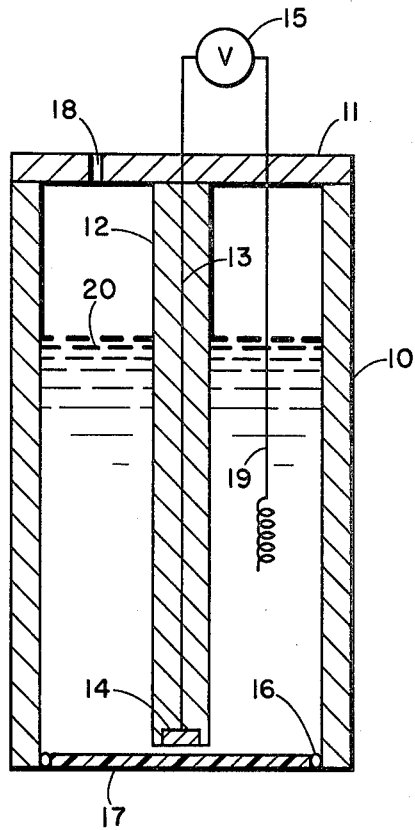

United States Patent [19]

Oberhardt

[11] 4,418,148

[45] Nov. 29, 1983

[54] MULTILAYER ENZYME ELECTRODE MEMBRANE

[75] Inventor: Bruce J. Oberhardt, Mishawaka, Ind.

[73] Assignee: Miles Laboratories, Inc., Elkhart, Ind.

[21] Appl. No.: 318,627

[22] Filed: Nov. 5, 1981

[51] Int. Cl.$^3$ ............... C12N 11/12; C12N 11/08; C12N 11/04; C12M 1/40

[52] U.S. Cl. ................... 435/179; 204/403; 435/14; 435/180; 435/182; 435/288

[58] Field of Search ............ 435/177, 179, 180, 182, 435/288, 14; 204/195 B, 1 T

[56] References Cited

U.S. PATENT DOCUMENTS

| | | | |
|---|---|---|---|
| 3,715,277 | 2/1973 | Dinelli et al. | 435/182 |
| 3,947,325 | 3/1976 | Dinelli et al. | 435/179 |
| 3,979,274 | 9/1976 | Newman | 435/14 X |
| 4,004,980 | 1/1977 | Emery et al. | 435/179 |
| 4,090,022 | 5/1978 | Tsao et al. | 435/179 X |
| 4,092,233 | 5/1978 | Clemens et al. | 435/14 X |

OTHER PUBLICATIONS

Kolarik et al., Glucose Isomerase Cells Entrapped in Cellulose Acetates, Immobilized Enzymes in Food and Microbial Processes, Plenum Press, N.Y., 1974 (pp. 71-83).

*Primary Examiner*—David M. Naff
*Attorney, Agent, or Firm*—Roger N. Coe

[57] ABSTRACT

A contiguous multilayer membrane for use with an electrochemical sensor is prepared comprising a first relatively nonporous dense polymer layer, a second polymer layer less dense and more porous than the first layer, a third layer containing an enzyme and a fourth polymer layer less dense and more porous than the first layer. The polymer is preferably cellulose acetate and the second and fourth layers are prepared with a solvent and nonsolvent for the polymer. The membrane may contain multiple enzyme layers separated by a polymer layer. The multilayer membrane provides advantages of higher substrate conversion, homogeneous distribution of enzyme and/or minimized interference with analyte diffusion.

15 Claims, 6 Drawing Figures

MULTILAYER ENZYME ELECTRODE MEMBRANE

This application is related to copending applications Ser. Nos. 318,625 and 318,626.

The present invention relates to a multilayer membrane suitable for use with an electrochemical sensor and a method of making said multilayer membrane. The membranes as described herein are used in voltametric cells for electrochemical analysis commonly known as polarographic cells and are referred to as such hereinafter. These cells comprise an enzyme for converting a substance which is an unknown to be measured into a material which can be measured by way of an electrical signal from the cells. A wide variety of assay techniques and sensors are available for the measurement of various materials. Of particular interest to the medical field, is the measurement of small amounts of various substances contained in body fluids, such as blood, in body tissues, in foodstuffs, and the like. Such substances include glucose, urea, uric acid, triglycerides, phospholipids, creatinine, amino acids, lactic acid, xanthine, chondroitin, etc. The development of a sensor for controlling or monitoring the glucose concentration in blood or other body fluids is important, particularly, for maintaining normal blood glucose levels in a diabetic patient. Typically, blood samples are withdrawn from the patient for an on-line analysis for glucose concentrations using a glucose oxidase electrode with a polarographic detector for the generated hydrogen peroxide. Customarily, such detectors comprise an enzyme electrode for the determination of hydrogen peroxide with an anode, a cathode, an electrolyte, and a membrane of specific composition containing an enzyme that has been immobilized.

Enzymes have been used in conjunction with polarographic cells in instances where the unknown substance to be measured is not electrochemically active itself, but by conversion or reaction of the enzyme with the unknown sample, a reaction product is obtained that may be measured; that is, it is detectable by polarographic means. As stated above, the most common problem of medical interest is the desire to measure glucose in the blood. The problem is that glucose is itself not electrochemically active. However, in the presence of the enzyme glucose oxidase the following reaction takes place:

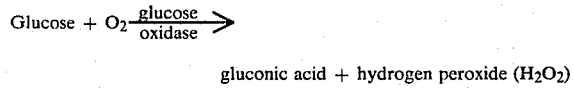

Glucose + $O_2$ $\xrightarrow{\text{glucose oxidase}}$ gluconic acid + hydrogen peroxide ($H_2O_2$)

The hydrogen peroxide that is generated by this reaction is measurable by a polarographic detector and therefore by appropriate calibration and calculations, it is possible to determine, from the amount of $H_2O_2$ liberated, what the glucose content was in the original specimen or sample.

Generally, a polarographic cell comprises an electrically insulating receptacle, an indicator or sensing electrode electrically contacting a membrane and a reference electrode which is electrically in contact with the membrane. By the expression "contacting" it is intended to include the situation where the contact between membrane and electrode is obtained directly or through a layer of electrolyte. Cells of various designs are widely known and understood in the art. Of particular interest for purposes of the invention is the cell shown in Clemens et al., U.S. Pat. No. 4,092,233.

In the prior art, in the case of an enzyme membrane structure, it is known to arrange a second hydrophilic membrane at a distance from the first mentioned membrane. In the space between the two membranes, a layer of concentrated enzyme is present. The free face of the second membrane provides the test surface to which the substrate to be tested is applied. This type of enzyme membrane is described in the Annals of the New York Academy of Science, Vol. 102 (1962), pages 29-49. In that article, it was suggested that a pH sensitive electrode could be used to detect gluconic acid produced by the reaction. It was disclosed that the enzyme in such a system could be trapped between two cellulose acetate membranes. Glucose diffuses through the membrane and is converted by the enzyme to gluconic acid which then diffuses both towards the pH sensitive glass and back into the donor solution.

The first mentioned membrane facing the sensing electrode is made up of a material which can be penetrated by the substance to which the sensing electrode is sensitive. For example, this membrane is permeable to the reactants of the enzymatic reaction but impermeable to the enzyme itself. It may be made of cuprophane but in the event that one of the reaction products is a gas at normal pressure and temperature and it is desired to measured via this gas, the membrane may consist of hydrophobic plastic impermeable to ions but slightly permeable to such gases as oxygen, carbon dioxide or ammonia. Numerous plastics having such properties are known including silicone rubber, tetrafluoroethylene and the like.

In a later type of polarographic cell developed by Clark and described in U.S. Pat. No. 3,539,455, the enzyme is placed on the electrode side of the membrane, and a platinum anode measures the hydrogen peroxide produced. Glucose, a low molecular weight species, passes through the membrane and reacts with the enzyme, but interfering high molecular weight substances such as catalase and peroxidase do not. It is disclosed that the enzymes may be held in a thin film directly between the platinum surface and the membrane by placing the enzyme on a porous film which has spaces large enough to hold enzyme molecules. However, cellophane membranes will not prevent low molecular weight interfering materials such as uric acid or ascorbic acid from reaching the sensing electrode. Clark suggested a dual electrode system to overcome that problem. The compensating electrode, without an enzyme present, gives a signal for the interfering substances while the enzyme electrode detects both the hydrogen peroxide and the interference. By calculation, the glucose level is determined. Such a dual sensor system, however, may encounter difficulties in the matching of the two cells.

It was then proposed to have an enzyme electrode which employs a thin filter membrane to prevent passage of low molecular weight interfering materials, such as uric acid and ascorbic acid, while permitting hydrogen peroxide to pass therethrough with minimum hindrance. There exist membrane materials, such as silicone rubber and cellulose acetate, which permit passage of hydrogen peroxide but which are effective barriers to interfering substances. Since this type of membrane must be placed between sensing electrode and some component of the sensing system, it follows that in order for measurement equilibrium to be as rapid as possible, the membrane must be as thin as possible while still retaining its selectivity. In the case of a hydrogen peroxide sensing probe, this membrane will need to be less than 2 microns thick. A membrane of this thickness is difficult to use in practice because of its insufficient strength.

The art then turned to depositing the material in a thin layer on a porous substructure to provide the necessary strength while at the same time being of little hindrance to hydrogen peroxide passage, and the weak interference rejecting layer can be thin to enhance speed of response.

In Newman, U.S. Pat. No. 3,979,274, a laminated two-ply membrane is described wherein an enzyme adhesive is used to bond the two-lies together. The membrane includes a support layer which controls substrate diffusion and serves as a barrier to high molecular weight substances, an enzyme preparation for reacting with the unknown and for bonding the layers together, and an essentially homogeneous layer that serves as a barrier to interfering low molecular weight materials but permits hydrogen peroxide to pass through. However in this development, it is necessary to make a sandwich consisting of two membranes with a layer of enzyme between, the enzyme acting as the adhesive or binding agent. In this type of arrangement, the use of too much enzyme could slow down the diffusion of the diffusing species to an unacceptable amount. If a thinner layer of enzyme is used, there is acceptable diffusion, but the loading of enzyme may not be adequate.

A still later development came in British Pat. No. 1,442,303 (Radiometer) wherein there was proposed a composite membrane which is an inhomogeneous membrane formed as a unit. The membrane has two different strata, one has a thickness of less than 5 microns and the other is sufficiently thick to provide strength. The enzyme is bonded to a surface of the membrane.

Other prior art has shown a number of disadvantages.

Thus, the method of Koyama et al., *Analytica Chemica Acta*, Vol. 116, pages 307–311 (1980), immobilizes glucose oxidase to a cellulose acetate membrane. This method is more time consuming; it involves more steps and suffers from the disadvantages that a monolayer of molecules would be the maximum possible enzyme load achievable.

Wingard et al., *The Journal of Biomedical Materials Research*, Vol. 13, pages 921–925 (1979) discloses a platinum screen or wire for immobilization of the enzyme. This would allow greater surface area to be utilized for binding than the method of Koyama et al. and hence could employ greater numbers of enzyme molecules. However, the approach of Wingard is also limited to a monolayer of enzyme and capable of sustaining high conversion rates of substrate diffusing through the open spaces in the platinum screen near the surface of the platinum wire only.

In accordance with the present invention, there is provided a multilayer membrane formed of a plurality of layers or strata of polymer and enzyme which function together to overcome problems that have occurred in the prior art. The multiple layer technique of the invention affords the opportunity to obtain the advantages of a distributed enzyme preparation through the utilization of more enzyme being present in the composite multiple layer structure without encountering the problems which have been observed in the use of single layer enzyme sandwich membranes of the past.

A significant advantage of the present invention resides in the fact that because the enzyme appears in more than one layer the overall distribution of the enzyme will appear to be homogeneous and thereby eliminate any inhomogeneity which may be present in any individual enzyme layer.

In addition, any significant interference with analyte diffusion which may be caused by unusual concentrations of enzyme in individual layers will be balanced by the total overall diffusion of the analyte through a multiplicity of enzyme containing layers where any discontinuities or high concentrations of enzyme will effectively be equalized.

The principles involved in the present invention may be illustrated with reference to the analysis of blood for glucose content. However, it should be noted that the present invention is applicable to use with many different enzyme systems, polymer membrane formulations, and the resulting multiple layer membranes may be used for analysis of numerous fluids for various components. The liquid portion of blood consists of proteins, lipids, and other substances. Nonelectrolytes are present such as glucose, enzymes such as catalase, electrolytes such as ascorbic acid (vitamin C) and various metallic salts made up of cations of sodium, potassium, magnesium, calcium, iron and copper, and anions such as chlorides, phosphates, bicarbonates, and carbonates. The phosphates, carbonates and bicarbonates operate as buffers to maintain the pH of blood at a fixed level under normal conditions. If a sample of blood were placed on one side of a membrane in a cell and an aqueous solution of, for example, the enzyme glucose oxidase and oxygen on the other side of the membrane, certain low molecular weight materials will pass from the blood through the membrane to the glucose oxidase solution. The high molecular weight materials such as the enzymes will not pass through the membrane. The rates of permeability of the various materials through the membrane are fixed because of the nature of the membrane. By selection of appropriate materials, the membranes may be designed to have a molecular cut off at any desired point; for example, at approximately 300. This means that materials of a molecular weight of greater than about 300 will not pass through.

Glucose, a low molecular weight material, will pass through such a membrane and react with the enzyme glucose oxidase in the presence of oxygen to form gluconolactone and hydrogen peroxide. Gluconolactone in the presence of water will hydrolyze spontaneously to form gluconic acid.

Gluconic acid and hydrogen peroxide, being relatively low molecular weight species compared to the enzyme glucose oxidase, will pass through such a membrane. Catalase and peroxidases which are large enzyme molecules capable of rapidly destroying $H_2O_2$ and which are present in biochemical fluids are prevented from passing through the membrane. The foregoing is given by way of illustration and it is to be understood that the present invention may be used with any suitable enzyme for analysis of various components in fluids.

According to the present invention, the multilayer membrane may be utilized in a cell for electrochemical analysis comprising, in general, an electrically insulating receptacle, an anode and a cathode as is shown in U.S. Pat. No. 4,092,223. The membrane of this invention may also be used in older type devices such as those of Clark, U.S. Pat. No. 3,539,455, utilizing a sensing electrode (anode), a reference electrode (cathode) in a space in the receptacle which is separated from the sensing electrode and adapted to hold an electrolyte. The membrane electrically contacts the electrodes; a path for an electrical current extends between anode and cathode or between the reference electrode and the sensing electrode and the membrane which is described herein.

Multilayer membranes of the invention are characterized by a plurality of layers or phases of polymer and a plurality of layers or phases containing enzyme. Since an intermingling or diffusion of the layers is believed to occur, the terms layers and phases are used interchangeably to mean layers which may interact at their interfaces. Typically, the multilayer membrane will include at least one relatively high density polymer layer, a plurality of relatively lower density polymer layers and enzyme containing layers. The several polymer layers thus described may be separated by a layer of enzyme.

It is a characteristic feature of the present invention that the multilayer membrane include as one of the two outer most layers, a layer of relatively dense polymer. This layer or outer stratum is formed by dissolving a suitable polymer in a solvent therefor and then casting the resulting solution on an appropriate surface. Illustratively, cellulose acetate in acetone may be mentioned in this regard. By dissolving the polymer in a solvent and casting a film thereof, there is obtained a layer or stratum which is relatively dense compared to the other polymer layers, which are cast from a dispersion of the polymer in a solvent/nonsolvent mixture. A skin comprised of dense polymer may be formed on the exposed surface of the less dense layer which functions to block the migration to the sensing electrode of interfering substances such as uric acid, ascorbic acid, and large nongaseous molecules and similar substances and allows the passing of solvent and low molecular weight species, for example, enzymatic conversion products such as hydrogen peroxide.

Although cellulose acetate is specifically mentioned as the polymer used for preparation of the dense polymer layer, a membrane exhibiting these properties can be made of other materials as well, such as copolymers of cellulose acetate and the like which are known in the art for membrane formation.

It has been determined that a reasonably short measuring time requires that the overall thickness of the multilayer membrane should not exceed, preferably, about 70 microns although this can vary depending on the kind of measurement to be carried out. It is to be understood that the several layers in the multiple layer membrane of the invention can vary widely in thickness. Thus, the dense layer may be relatively thin compared with the less dense, more porous polymer layer. They may also be of equal thickness. Generally, the more dense layer will not be thicker than the less dense, more porous layer, although under certain conditions, the porous layer may be thinner than the dense layer.

Figure 2:
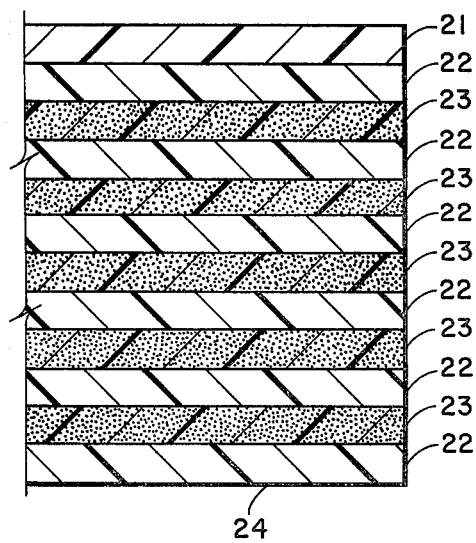
Figure 3:
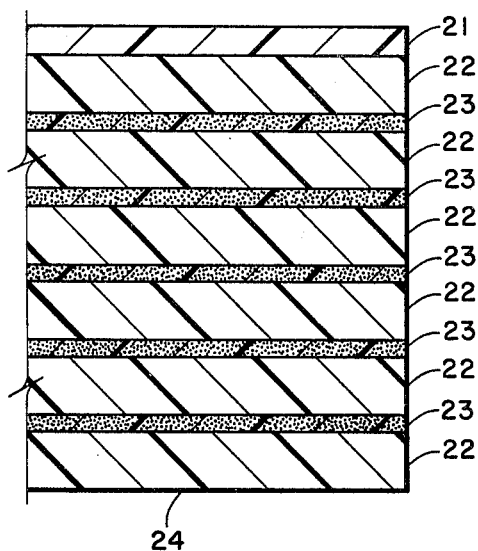
Figure 3A:
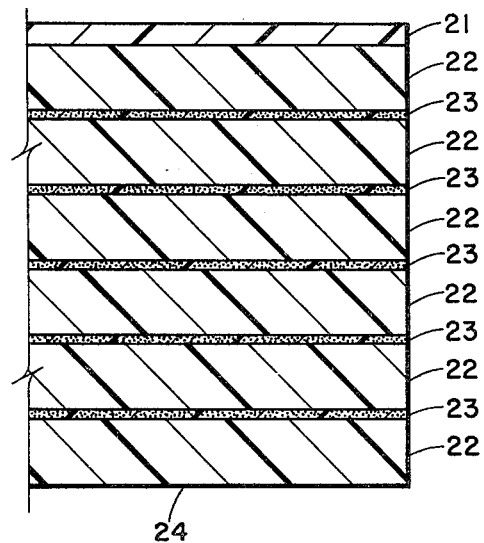
Figure 3B:
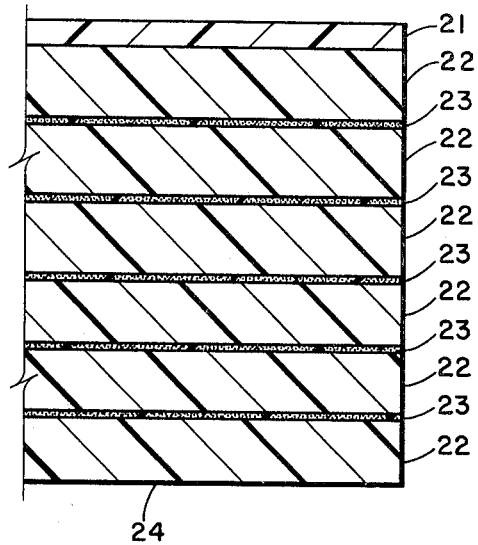
Figure 4:
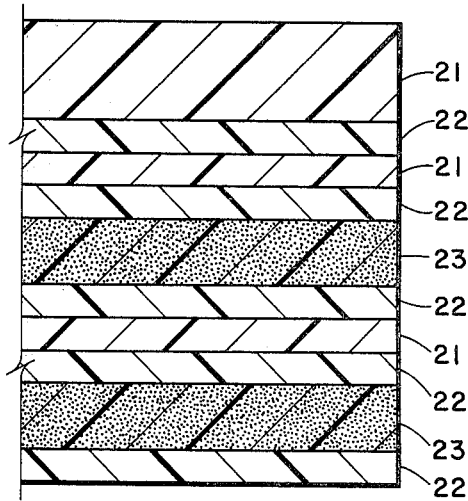

The invention will be further understood with reference to the drawings wherein:

FIG. 1 is a vertical partial section view of an older type polarographic cell which may utilize the membrane of the invention, FIG. 2 is a cross-section view, considerably enlarged and not to scale, of a multilayer membrane of the invention, FIGS. 3 (a, b and c) is a cross-section view of three other embodiments of a multilayer membrane of the invention; and FIG. 4 is a cross-section view of another embodiment of a multilayer membrane of the invention.

In forming the multilayer membrane according to the invention, multilayer film forming equipment as is used in the photographic film industry can be used. The membrane consists of a multiplicity of phases which are not necessarily distinct but which when cast separately and independently of each other are characterized as several relatively porous, phases in the multilayer, and in the final multilayer membrane a relatively nonporous, denser phase which in the multilayer membrane faces the sample; e.g., the blood specimen. For purposes of this description, this dense layer will be referred to as the outer most layer of the membrane.

In the multilayer membrane, the porosities and thicknesses of the various components or strata may become modified as they are fused together. In general, there is a diffusion zone at the boundary of two adjacent strata. The relatively dense layer is formed of polymer as is the more porous, less dense layer. In between the individual polymer strata there is disposed a layer containing enzymes. Additionally, there may be distributed uniformly throughout the relatively porous polymer phase, a particulate dispersed enzyme or a protectively encapsulated enzyme. This enzyme may, however, be distributed throughout the multilayer membrane. The individual properties of the phases or layers forming the multilayer membrane, if cast separately should be as follows: the relatively nonporous dense polymer phase should if cast by itself and tested have a molecular weight cut off at a specific point; e.g., approximately 300; the highly porous polymer phase if cast by itself and tested should freely pass the substrate for the enzyme (at the surface adjacent to the surface onto which it has been cast) and yet exclude macromolecules such as large proteins.

In order to achieve desired properties for detection of analyte, the membrane of the invention is fabricated in a multi-stage process. For example, the relatively dense membrane, or first component, is formed by casting or spreading a solution of an appropriate polymer, such as cellulose acetate in a solvent therefor; e.g., acetone, on a suitable surface which does not interact with or bond to the membrane. Representative surfaces to provide a support for the cast film are glass and some plastics such as polyethylene. The film is cast with conventional film forming equipment, well known in the art, whereby it is possible to control the thickness of the resulting film. After being spread on the surface, the cast film may be dried. This thin film serves as the relatively nonporous phase and may also be thin, relative to the more porous phase. The thickness of this phase generally ranges from 2 to 5 microns, although the dimension of the film is not critical for purposes of the invention.

A plurality of relatively more porous strata are prepared by casting a film by dissolving a suitable polymer in a solvent mixture therefore. The solvent mixture used to form the more porous layer includes a solvent for the polymer and a nonsolvent for the polymer. The solvent mixture used is such as to be capable of phase inversion to form pores.

A phase inversion type of polymer layer can be formed in this way and may be then cast directly on top of the relatively more dense layer. Since both casting solutions may be of the same polymer base, and preferably use the same solvent, there may be formed a diffusion zone of the two at the interface or boundary and no clear distinction can be made between the two phases. Indeed, the order of casting may also be reversed, although it is preferred to cast the more dense film first. The first film need not be absolutely dry when the second film is cast on it; i.e., the first film may be tacky to the touch. It is believed that a skin forms on the top of the film after drying.

The solution of the polymer such as cellulose acetate for the formation of the first component, or more dense layer is formed by dissolving a cellulose acetate polymer in an inert organic solvent such as a ketone. Typical ketone solvents are acetone, cyclohexanone, methylethylketone and the like. Mixtures of miscible solvents may also be used. Concentrations of the polymer in solvent may vary, as from 1 to 5%, preferably 2 to 3%. The film is cast with any suitable film applicator such as will product a final product film thickness of 1-10 microns, preferably 2-5 microns in thickness.

The phase inversion member or second type of layer present; that is the relatively porous portion of the multilayer membrane of this invention, is prepared by forming a cellulose acetate, or other suitable polymer solution in an inert organic solvent such as a ketone. A nonsolvent or nonsolvent mixture for the polymer is then mixed with the polymer solvent solution. The particular polymer such as cellulose acetone and the particular nonsolvent; e.g., ethanol and water, is not critical and others may be used. When using cellulose acetate as the polymer, lower alcohols mixed with water are usually preferred for this purpose.

According to the invention, a plurality of less dense polymer layers are provided in the multilayer membrane each of which layers is separated from the next adjacent layer by an intermediate layer of enzyme. The enzyme layer may be formed by aqueous solutions or suspensions of enzyme which may contain additives to facilitate spreading. Generally, the outer most or top layer is the relatively dense layer which has coated on one side or surface thereof a layer of less dense or porous polymer layer. Then, the next layer may be an enzyme layer followed by another layer of porous polymer followed by another layer of enzyme, etc.

As described herein, the layer technique affords the opportunity to obtain the advantages of a distributed enzyme preparation through the utilization of more enzyme in the overall membrane structure and thereby obtain a higher substrate conversion rates. This may be accomplished without suffering from the previously acknowledged drawbacks of prior art layering of the enzyme. These drawbacks include any inhomogeneity; i.e., gaps or spaces in some areas and aggregates of enzyme in others, and interference with the transport of analyte species by blockage of diffusion in areas of aggregated enzyme. With the repitition of enzyme layers in the multilayer membrane of the invention, if any inhomogeneous distribution of enzyme appears on the microscopic level, in any one layer of enzyme, this will on the average equalize or distribute itself in a homogeneous way at the macroscopic level. As a result of the multiple layers of enzyme, there will be achieved an essentially equal amount of enzyme per unit area of membrane which considered from the plane parallel to the major axis of the membrane surface.

Any interference with analyte diffusion in regions of enzyme concentration in any one layer of enzyme can be minimized by using a multiplicity of thinner layers of enzyme. At the same time, larger amounts of enzyme may be incorporated in the total membrane, than is the case if one thicker, discrete enzyme layer were utilized.

As will be seen from the drawings, the number and thicknesss of the individual layers may be varied for desired transport and system response characteristics, e.g., see FIG. 3. Moreover, it should be apparent that a variety of enzymes may be used in one multilayer membrane.

Also, various film thickness and combinations of phases of dense and less dense membranes may be utilized to obtain a range of film porosity properties not easily obtainable by using one or two layers alone, See FIG. 4.

In certain situations, enzymes may be adversely affected by the solvents with which they come into contact. Hence, particularly in those instances where enzyme sensitivity is a problem, the present invention offers an advantage.

Greater protection may be afforded to the enzyme from damage by the solvent (e.g., acetone) for the membrane forming polymer (e.g., cellulose acetate) than in the case where the enzyme may be in contact with the solvent. This is because adjacent layers may be formed in a cascading sequence such that prior layers are completely or partially soldified before subsequent layers are applied.

To further ensure protection of solvent sensitive enzymes, the enzyme may be microencapsulated according to the teachings of my copending patent application Ser. No. 318,625, filed on even date herewith, and entitled "Enzyme Electrode Membrane Wherein Enzyme is Protectively Encapsulated," especially if additional protection is desired from solvents in adjacent layers. Said patent application is incorporated herein by reference.

Typical electrochemical sensors which can be employed with the membrane of this invention include the BIOSTATOR glucose electrode of Miles Laboratories, Inc. See U.S. Pat. No. 4,092,233.

The overall thickness of the membrane of the invention can vary from about 40 to about 100 microns, but is preferably approximately 70 microns. The more dense layer ranges from 2 to about 5 microns and the less dense individual layer range from about 2 to 20 microns. Variation in these values is permissible within the contemplation of this invention as the precise thickness of the layers can range widely as will be seen by reference to the drawings. The preferred membrane is about 70 microns in thickness.

Referring to FIG. 1, there is shown a polarographic cell assembly which includes a receptacle in the form of an electrically insulating container 10 made of a plastic or glass material or any other suitable material and which may be of any cross-sectional area and shape, but is preferably cylindrical. This is covered by an electrically insulating cap 11. Positioned within the receptacle is an electrically insulating member rod, or cylindrical column 12, which contains in it an electrical conductor 13. This conductor is connected to an active or exposed element 14 which may be platinum, gold, silver, graphite or the like.

A lead is attached to the electrode which passes through the rod or column and through the cap to be connected with a D.C. voltage source 15.

The lower end of the receptacle is provided with a support means 16 such as a ring or retainer and the membrane 17 in accordance with the present invention is supported over the end of the supporting receptacle nearest the central electrode and spaced a capillary distance from the active face of the electrode. The membrane can be held in position with any suitable means, for example, by an O-ring fitting into a circular groove or other convenient means in the receptacle. A current measuring instrument (not shown) is connected in series with the cell.

Typically, the receptacle is provided with a vent 18 to permit gases to escape if pressure inside the receptacle rises to a sufficiently high degree.

An annular space is provided between the central rod and the receptacle walls and receives a reference electrode 19 which may be for example, silver chloride coated silver wire. The space 20 inbetween is at least partially and preferably completely filled with a liquid mixture of electrolyte which may be introduced into the chamber through an aperture.

In polarographic measurements, two electrodes are commonly used, one of which is polarized and does not allow current to flow until depolarized by the substance being measured. In the cell structure shown in FIG. 1, electrode 19 is the cathode and is polarized and frequently referred to as the reference electrode. The other electrode, electrode 14 as shown in FIG. 1, functions as an anode and is not polarized in the presence of the substance being measured and therefore will not restrict the flow of relatively large current and is frequently referred to as the sensor electrode. The electrodes shown in FIG. 1 are in an electrically insulating relation and the electrolyte material which occupies the chamber provides a conductive path between the two electrodes. Typical electrolytes include sodium or potassium chloride, buffers including carbonates, phosphates, bicarbonates, acetates, alkali or rare earth salts or other organic buffers or mixtures thereof may be used. The solvent for such an electrolyte may be water, glycols, glycerine and mixtures thereof as is well known in the art.

FIG. 2 shows a multilayer membrane in cross-sectional detail. A dense layer 21 and a plurality of less dense or porous layer 22 comprise the strata which less dense layers are separated by a layer of enzyme 23. The enzyme layer 23 is shown in FIG. 2 as being of the same thickness as the dense layer 21 and the porous layer 22. However, as shown in FIG. 3, these layers may be different. They may also be different chemically in addition to being different in physical dimensions. Some of the enzyme may diffuse into the adjacent layers during preparation of the membrane if the solvent for the cellulose acetate has not yet fully evaporated. Membrane surface 24 is in electrical contact with the electrode. The outer free surface of layer 21 represents the test surface which is to be brought into contact with the solution to be analyzed.

As shown in FIG. 4, the multilayer membrane may include several layers of the dense strata as well as several layers of enzyme 23 and porous layer 22.

The membrane of the invention may be produced by initially casting the relatively dense polymer layer, stratum or film onto a suitable surface and permitting it to at least partially dry. This first layer is referred to as the first component of the multilayer membrane. If this dense layer is omitted, the measurements may be more subject to nonlinearity due to oxygen depletion which is, in turn, caused by an increased flux of glucose molecules transported through the membrane and reacting with enzyme.

The porous phase inversion type polymer layer which is referred to as the second component may be cast directly on top of the thin layer. It may be possible to first cast the porous portion of the membrane and then cast the dense portion directly on top of it. The phase inversion member or more porous portion of the membrane composite may be formed by providing a solution of the polymer in an inert organic solvent such as acetone. The solution is then mixed with a nonsolvent for the polymer. Suitable nonsolvents include alcohol and water mixtures. In the case of cellulose acetate, ethanol and water is a suitable nonsolvent.

The third component of the multilayer membrane comprises the enzyme containing layer. Typically, this is formed of an aqueous solution or suspension of the enzyme, which may further contain additives to facilitate spreading.

As a fourth component another phase inversion porous polymer layer may be utilized.

A fifth layer of enzyme containing substance is then also utilized. The multilayer membrane of the invention thus contains at least one first component; i.e. a relatively dense polymer layer and at least two phase inversion type polymer layers; that is, a porous layer of the second type. In addition, the membrane contains at least two layers of enzyme material. Preferably, the membrane of the invention contains at least 3 or 4 enzyme layers and 3 or 4 porous polymer layers.

In preparing the membranes of the invention, the sequence of forming layers may be carried out according to the process steps stated above and thereby produce a membrane as shown, for example, in FIGS. 2 or 3. Or, the sequence may be varied to produce a structure such as shown in FIG. 4.

Typically, the mixing of enzyme should take place at low temperatures; i.e., 0° C. or below 0° C. The time of mixing is also to be minimized in order to avoid inactivating the enzyme.

The following specific example illustrates how the invention may be carried out but should not be considered as limiting thereof in any way.

EXAMPLE

On a clean glass plate, spread a 3% cellulose acetate in acetone solution with 2 mil film applicator to prepare the dense film portion.

Prepare the phase invention cellulose acetate casting solution by mixing 1.5 cc of ethanol with 5 cc of a 10% cellulose acetate in acetone solution. This is then placed in a salt water ice bath and stirring of the solution is continued.

The second solution which will form the porous layer is then spread on top of the first membrane with an 18 mil applicator. The spread film is then permitted to dry for several hours at room temperature.

The enzyme layer can be cast on top of the porous layer at any convenient time such as when the surface of the film is tacky to the touch, or partially dry.

The enzyme preparation may simply be a mixture of the appropriate enzyme such as glucose oxidase in water. For example, 1.0 cc of an aqueous glucose oxidase solution may be used. This solution contains 2,000 to 3,000 units of the glucose oxidase per cc of solution. Of course, other materials such as a binder or cross-linking agent like glutaraldehyde may be included in the enzyme preparation. Likewise, the proportion of enzyme to water in the preparation is immaterial as long as a flowable paste or solution is formed which may be easily coated or deposited. Sufficient enzyme is incorporated into the solution to prepare an adequate reactive amount for measurement.

The foregoing procedure of casting the polymer films and enzyme layers is then repeated until the multilayer membrane including at least 1 dense layer, and at least two porous and enzyme layers are obtained. Preferably, the product contains at least 3 or 4 layers of enzyme and at least 3 or 4 layers of porous film.

The multilayer membrane of the present invention is a self-supporting film of a total thickness which may range from about 50 to 100 microns, preferably about 70 microns. The multilayer membrane may be shaped to any particular configuration or size or may be cut or dimensioned in any particular way to fit receptacles for polarographic cells or electrodes of any suitable dimension. It may, in particular, be fastened to an O-ring for use in an electrode such as described in U.S. Pat. No. 4,092,233.

To fasten the membrane to a rubbery O-ring of an appropriate size, a gluing operation may be employed. The membrane may also be cast directly onto an electrode surface.

In addition to cellulose acetate, other polymers capable of being dissolved in solvents and undergoing phase inversion with the addition of a weak solvent or nonsolvent would be potential membrane materials. Such polymers include cellulose nitrate, ethylcellulose and other cellulose derivatives. In addition, polycarbonate is a suitable alternative if methylene chloride is employed as a solvent instead of acetone or other ketones.

As a substitute or alternative for the lower alcohols present in the phase inversion mixture formamide can be used.

Further variations and modifications of the invention as will be apparent to those skilled in the art after reading the foregoing are intended to be encompassed by the claims that are appended hereto.

We claim:

1. A method of making a contiguous multilayer membrane of about 40 to about 100 microns in overall thickness suitable for use with an electrochemical sensor in the measurement of an unknown which comprises:

providing as a first layer, a polymer dissolved in an inert organic solvent and casting said polymer in solution onto an inert support surface which is unreactive with said polymer and does not form a bond to said polymer;

permitting said solution to form a film and thereby obtaining a first relatively nonporous dense polymer layer of about 2 to about 5 microns in thickness;

providing as a second layer, a composition comprising a polymer dissolved in an inert organic solvent, mixing said polymer dissolved in solvent with a nonsolvent for said polymer to obtain a dispersion and thereafter casting said dispersion onto said first layer and thereafter permitting said second layer to dry to form a porous polymer layer of about 2 to about 20 microns in thickness and less dense and more porous than the first layer;

providing a third layer comprising an enzyme solution or suspension and depositing said third layer onto the exposed surface of the second layer;

providing as a fourth layer, a composition comprising a polymer dissolved in an inert organic solvent, mixing said polymer dissolved in solvent with a nonsolvent for said polymer to obtain a dispersion and thereafter casing said dispersion onto the exposed surface of the third layer to provide a fourth porous polymer layer of about 2 to about 20 microns in thickness and less dense and more porous than the first layer; and thereby forming said contiguous multilayer membrane.

2. The method of claim 1 wherein each of said layers is deposited one or more times in sequence to obtain a multilayer membrane.

3. The method of claim 1 wherein the polymer is cellulose acetate or a copolymer of cellulose acetate.

4. The method of claim 1 wherein the inert organic solvent is a ketone.

5. The method of claim 1 wherein said second layer further includes an enzyme homogeneously dispersed therein.

6. The method of claim 1 wherein said second layer further contains an enzyme protectively encapsulated therein.

7. The method of claim 1 wherein said second layer is a phase inversion layer containing pores formed by dissolving said polymer in a solvent mixture, including a solvent and a nonsolvent for said polymer.

8. The method of claim 1 wherein the enzyme is glucose oxidase.

9. A method of making a contiguous multilayer membrane of about 40 to about 100 microns in overall thickness suitable for use with an electrochemical sensor in the measurement of an unknown which comprises:

(a) providing a first cellulose acetate polymer dissolved in an inert organic solvent;

(b) casting said first polymer in solution onto an inert support surface which in unreactive with said cellulose acetate and does not form a bond to said cellulose acetate;

(c) permitting said first polymer in solution to form a film and thereby obtain a first relatively nonporous dense layer of cellulose acetate of about 2 to about 5 microns in thickness;

(d) providing a second cellulose acetate polymer dissolved in an inert organic solvent mixing said second polymer with a nonsolvent for said polymer to form a dispersion thereof;

(e) casting said second cellulose acetate polymer dispersion onto said first layer of cellulose acetate and permitting said cellulose acetate polymer to form a porous second cellulose acetate layer of about 2 to about 20 microns in thickness and less dense and more porous than the first layer;

(f) providing an aqueous solution or suspension of an enzyme and depositing said enzyme in a layer onto the surface of said second polymer; and (g) repeating (d), (e) and (f) at least once to deposit at least one additional said second cellulose acetate layer and at least one additional enzyme layer;

thereby forming said contiguous multilayer cellulose acetate polymer membrane.

10. The method of claim 9 wherein the inert organic solvent used with said first and second cellulose acetate polymer is the same.

11. The method of claim 10 wherein the inert organic solvent is a ketone.

12. The method of claim 10 wherein the inert organic solvent is acetone.

13. The method of claim 9 wherein the enzyme is glucose oxidase and is present in a mixture of water and ethanol.

14. In a polarographic cell structure for use in electrochemical analysis of an unknown comprising an electrically insulating receptacle an electrode means mounted in said receptacle, and a membrane means, the improvement which comprises utilizing the multilayer membrane produced by the method of claim 1 or 9.

15. A multilayer membrane produced by the method of claim 1 or 9.

* * * * *